(12) United States Patent
Lee

(10) Patent No.: US 10,661,041 B2
(45) Date of Patent: May 26, 2020

(54) INFANT AND CHILD BONNET

(71) Applicant: GaleMed Corporation, Yilan County (TW)

(72) Inventor: Gary C. J. Lee, Yilan County (TW)

(73) Assignee: GALEMED CORPORATION, Yilan County (TW)

( * ) Notice: Subject to any disclaimer, the term of this patent is extended or adjusted under 35 U.S.C. 154(b) by 441 days.

(21) Appl. No.: 15/384,313

(22) Filed: Dec. 19, 2016

(65) Prior Publication Data

US 2018/0093060 A1    Apr. 5, 2018

(30) Foreign Application Priority Data

Sep. 30, 2016   (TW) .............................. 105214954 U

(51) Int. Cl.
| | | |
|---|---|---|
| *A42B 1/04* | (2006.01) | |
| *A61M 16/06* | (2006.01) | |
| *A42B 1/24* | (2006.01) | |

(52) U.S. Cl.
CPC ......... *A61M 16/0694* (2014.02); *A42B 1/045* (2013.01); *A42B 1/24* (2013.01); *A61M 16/0666* (2013.01); *A61M 16/0683* (2013.01); *A61M 2202/0208* (2013.01); *A61M 2240/00* (2013.01)

(58) Field of Classification Search
CPC ...... A41D 11/00; A42B 1/04; A61M 16/0465; A61M 16/0497; A61M 16/06; A61M 16/0605; A61M 16/0627; A61M 16/0633; A61M 16/0683; A61M 16/0694; A61M 3/027; A61M 2005/1586; A61M 25/02; A61M 2025/0206; A61M 2025/0213; A61M 2025/024; A61M 2025/0253; A61M 2025/026; A61M 16/0666–0677; G02C 3/02
USPC .......................... 224/181, 219, 222; 351/155
See application file for complete search history.

(56) References Cited

U.S. PATENT DOCUMENTS

| | | | | |
|---|---|---|---|---|
| 4,836,200 A | * | 6/1989 | Clark .................... | A61M 25/02 128/204.18 |
| 4,944,310 A | * | 7/1990 | Sullivan ................ | A61M 16/00 128/205.25 |
| 5,755,366 A | * | 5/1998 | Mazzo ..................... | A45C 1/04 150/131 |
| 6,889,689 B1 | * | 5/2005 | Neuman ........... | A61M 16/0683 128/201.22 |
| 2003/0047185 A1 | * | 3/2003 | Olsen .................... | A61M 16/06 128/203.22 |
| 2005/0061326 A1 | * | 3/2005 | Payne, Jr. ................ | A61F 5/56 128/206.11 |

(Continued)

*Primary Examiner* — Bhisma Mehta
*Assistant Examiner* — William R Frehe
(74) *Attorney, Agent, or Firm* — Chun-Ming Shih; HDLS IPR Services

(57) ABSTRACT

An infant and child bonnet for securing a breathing tube includes a cap body and an elastic fixing band. The cap body includes a first opening and a second opening corresponding to each other and includes a first connection portion. The elastic fixing band is connected to the cap body. One end of the elastic fixing band includes a second connection portion flexibly fixing the breathing tube. The second connection portion is joined to the first connection portion. Accordingly, the infant and child bonnet suits various head sizes and shapes and effectively fixes the breathing tube without displacement or detachment.

9 Claims, 3 Drawing Sheets

(56) References Cited

U.S. PATENT DOCUMENTS

| | | | |
|---|---|---|---|
| 2005/0081858 A1* | 4/2005 | Raje | A61M 16/0875 128/206.21 |
| 2006/0081250 A1* | 4/2006 | Bordewick | A61M 16/0666 128/206.11 |
| 2006/0218702 A1* | 10/2006 | Santos | A61M 16/0683 2/422 |
| 2006/0283456 A1* | 12/2006 | Geiselhart | A61M 16/06 128/206.24 |
| 2007/0106170 A1* | 5/2007 | Dunseath, Jr. | A61B 5/0478 600/544 |
| 2009/0299294 A1* | 12/2009 | Pinkus | A61M 25/02 604/177 |

* cited by examiner

INFANT AND CHILD BONNET

TECHNICAL FIELD

The present invention relates to an infant and child bonnet and, in particular, to an infant and child bonnet suits various head sizes of an infant/child and can effectively fix the breathing tube without displacement or detachment.

BACKGROUND

A continuous positive airway pressure (CPAP) delivery system is extensively utilized for noninvasive assisted ventilation (NAV) of patients like premature infants or neonates having neonatal respiratory distress syndrome. Since improper fixation of CPAP tubing may cause nasal pressure sores (i.e. bedsores resulting from undue pressure or friction on skin, sometimes even harming subcutaneous tissues, muscles and bones), and slippage of the tubing can cause inferior assisted breathing, a longer treatment period (more days in hospital), apnea or bradycardia associated with oxygen desaturation of the premature infants.

CPAP effectively reduces failures in removing an inserted tracheal tube, and can serve as a substitute for endotracheal intubation and mechanical ventilation, thereby causing a lower risk of medical complications resulting from the mechanical ventilation. Proper pressure is the key to successful treatment, and in order to provide a proper pressure, the tubing should be connected and fixed tightly. So far there are no suitable tubing securing bonnets for infants and young children, and hence the tubing is usually fixed by elastic bandage. Since the infant/child moves from time to time, it causes slippage or undesired folding of the tubing, leading to ineffective treatment. This problem is typically remedied by fixing the tubing more tightly. This approach, however, causes pressure sores on the skin of the infant's or the child's face/head.

Accordingly, it is the aim of the present invention to solve the above-mentioned problems. The present invention can prevent slippage of nasal tubing, reduce a risk of heart and lung complications resulting from slippage of the tubing, and greatly reduce the time and labor for fixing the tubing.

SUMMARY

It is an object of the present invention to provide an infant and child bonnet, which can suit various head sizes and can effectively fix the breathing tube without displacement or detachment.

Accordingly, the present invention provides an infant and child bonnet for securing a breathing tube. The infant and child bonnet comprises a cap body and an elastic fixing band. The cap body includes a first opening and a second opening corresponding to each other, and includes a first connection portion. The elastic fixing band is connected to the cap body. One end of the elastic fixing band includes a second connection portion flexibly fixing the breathing tube. The second connection portion is joined to the first connection portion.

According to one embodiment, the cap body further includes an accommodating space communicating with the first opening and the second opening.

According to one embodiment, a head of an infant or a child is inserted into the accommodating space from the first opening, the accommodating space suits various head sizes and shapes, and a size of the first opening is bigger than or the same to a size of the second opening.

According to one embodiment, the elastic fixing band is stitched in place between the first opening and the second opening.

According to one embodiment, wherein the second connection portion is disposed corresponding to the first connection portion of the elastic fixing band.

According to one embodiment, the cap body further includes a chin band, and the chin band is flexibly connected to a bottom of the cap body.

According to one embodiment, the chin band is integrally formed with the cap body.

According to one embodiment, the infant and child bonnet further includes an elastic tying band disposed adjacent to the second opening for tying the cap body.

According to one embodiment, the first connection portion and the second connection portion are male-female Velcro fasteners, male-female adhesive strips, male-female buckles, or male-female snap fasteners.

According to one embodiment, the cap body is made of knitted wool or knitted threads.

The present invention has the following advantages. The cap body can wrap the head of an infant/child and only expose a face of the infant/child. An upper portion of the cap body can be selectively tied by the elastic fixing band. Therefore, the infant and child bonnet is prevented from falling off or slipping off head. In addition, the infant and child bonnet is comfortable to wear and can keep the head of the infant/child warm.

The chin band of the present invention is connected in an integral manner or in a separate manner to a bottom (i.e. the first opening) of the cap body. The chin band further fixes the cap body on the head of the infant/child. In addition to that, the chin band helps to close a mouth of the infant/child to prevent leakage of oxygen from the mouth, thereby facilitating efficient treatment.

BRIEF DESCRIPTION OF THE DRAWINGS

The disclosure will become more fully understood from the detailed description, and the drawings given herein below is for illustration only, and thus does not limit the disclosure, wherein.

DETAILED DESCRIPTION

Detailed descriptions and technical contents of the present invention are illustrated below in conjunction with the accompany drawings. However, it is to be understood that the descriptions and the accompany drawings disclosed herein are merely illustrative and exemplary and not intended to limit the scope of the present invention.

Figure 1:
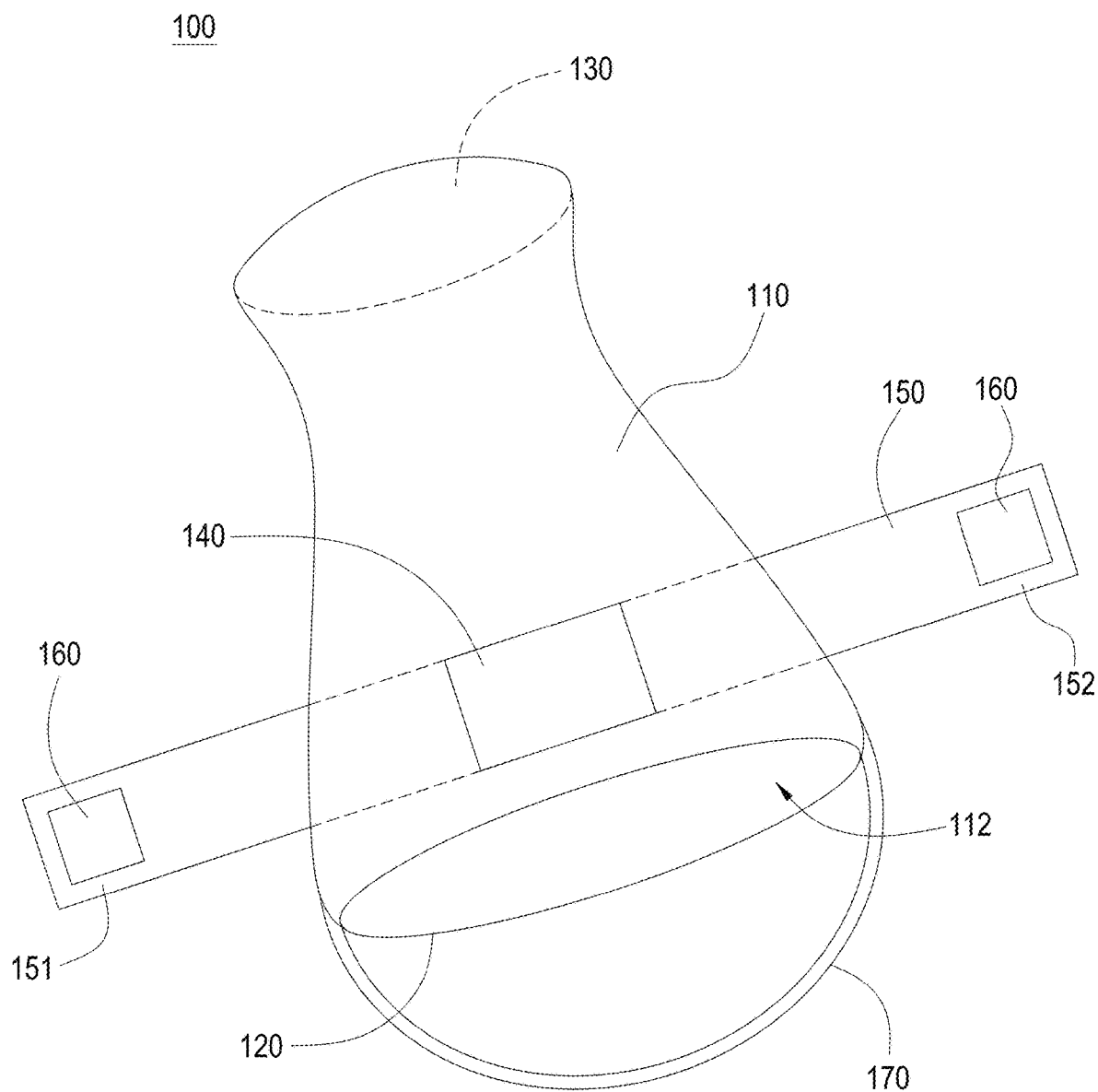
FIG. 1 is a perspective view of the present invention, illustrating an infant and child bonnet.
Figure 2:
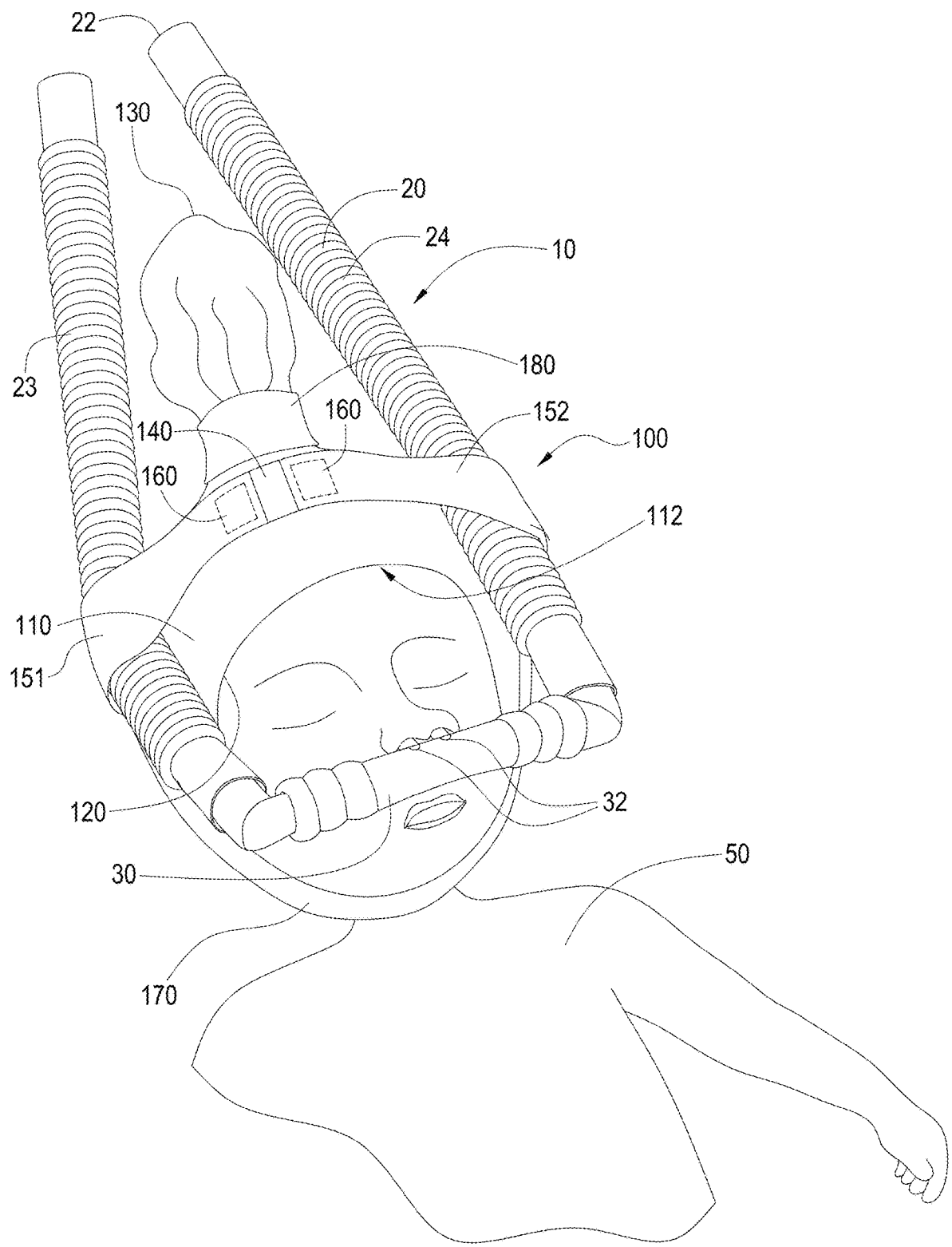
FIG. 2 is a schematic view, illustrating the infant and child bonnet according to a first embodiment of the present invention.

Referring to FIGS. 1 and 2, the present invention provides an infant and child bonnet 100 for securing a breathing tube 10. The breathing tube 10 in FIG. 2 includes two inlet tubes 20, a first inlet tube 23 and a second inlet tube 24, and a nasal tube 30 connected to the first inlet tube 23 and the second inlet tube 24. Oxygen enters from an inlet hole 22 of each inlet tube 20 and is discharged from two outlet holes 32 of the nasal tube 30, so that an infant or a child can inhale the oxygen easily. The present invention is not limited to any connection configuration or any particular number of the breathing tube 10 disclosed in the present embodiment.

The infant and child herein referred to includes, but not limited to, a newborn baby, an infant, a young child, or any older child who can wear the infant and child bonnet 100. In detail, the infant is from the birth to about one year old, a young child is from one year old to about five years old, an older child is from six years old to about twelve years old.

The infant and child bonnet 100 includes a cap body 110 and an elastic fixing band 150. The cap body 110 includes a first opening 120 and a second opening 130 corresponding to each other and includes a first connection portion 140. As shown in FIG. 1, the cap body 110 further includes an accommodating space 112 communicating with the first opening 120 and the second opening 130. The cap body 110 is preferably made of knitted wool or knitted threads or other suitable fabrics. The cap body 110 has elasticity, so a head of the infant/child 50 can be inserted into the accommodating space 112 from the first opening 120, and the accommodating space 112 suits various head sizes and shapes of the infant/child 50.

A size of the first opening 120 is preferably bigger than a size of the second opening 130 to facilitate the infant/child 50 to put on the infant and child bonnet 100 on his/her head. However, in other different embodiment, the size of the first opening 120 can be the same with the size of the second opening 130; configuration may vary as required.

The elastic fixing band 150 is stretchable, elastic, and is connected to the cap body 110. The elastic fixing band 150 can be an elastic bandage, a polybutylene terephthalate (PBT) elastic bandage, a cotton gauze bandage, or other suitable elastic band. One end of the elastic fixing band 150 is disposed with a second connection portion 160 for flexibly fixing the breathing tube 10, and the second connection 160 is joined with the first connection portion 140.

The elastic fixing band 150 is preferably stitched in place between the first opening 120 and the second opening 130. The elastic fixing band 150 includes a first arm 151 and a second arm 152. The first connection portion 140 in FIG. 1 is preferably disposed adjacent to an edge of the first opening 120, so that the second connection portion 160 on the elastic fixing band 150 can be correspondingly joined with the first connection portion 140. However, the first connection portion 140 can be selectively disposed on other place on the cap body 110; the present invention is not limited in this regard.

In the embodiment shown in FIGS. 1 and 2, the first connection portion 140 and the second connection portion 160 preferably are male-female Velcro fasteners or male-female adhesive strips, i.e. so-called nylon hook and loop fasteners. The nylon hook and loop fasteners are two fiber-based fastening components, one component has a loop structure while the other component has a hook structure. When the two components are pressed together, the hook structure and the loop structure are connected to each other to achieve temporary securement. When it is desired to separate the two components, the temporary securement can be broken simply by pulling the two components apart. Such fasteners can be repeatedly used, and it is convenient and simple to use them.

Figure 3:
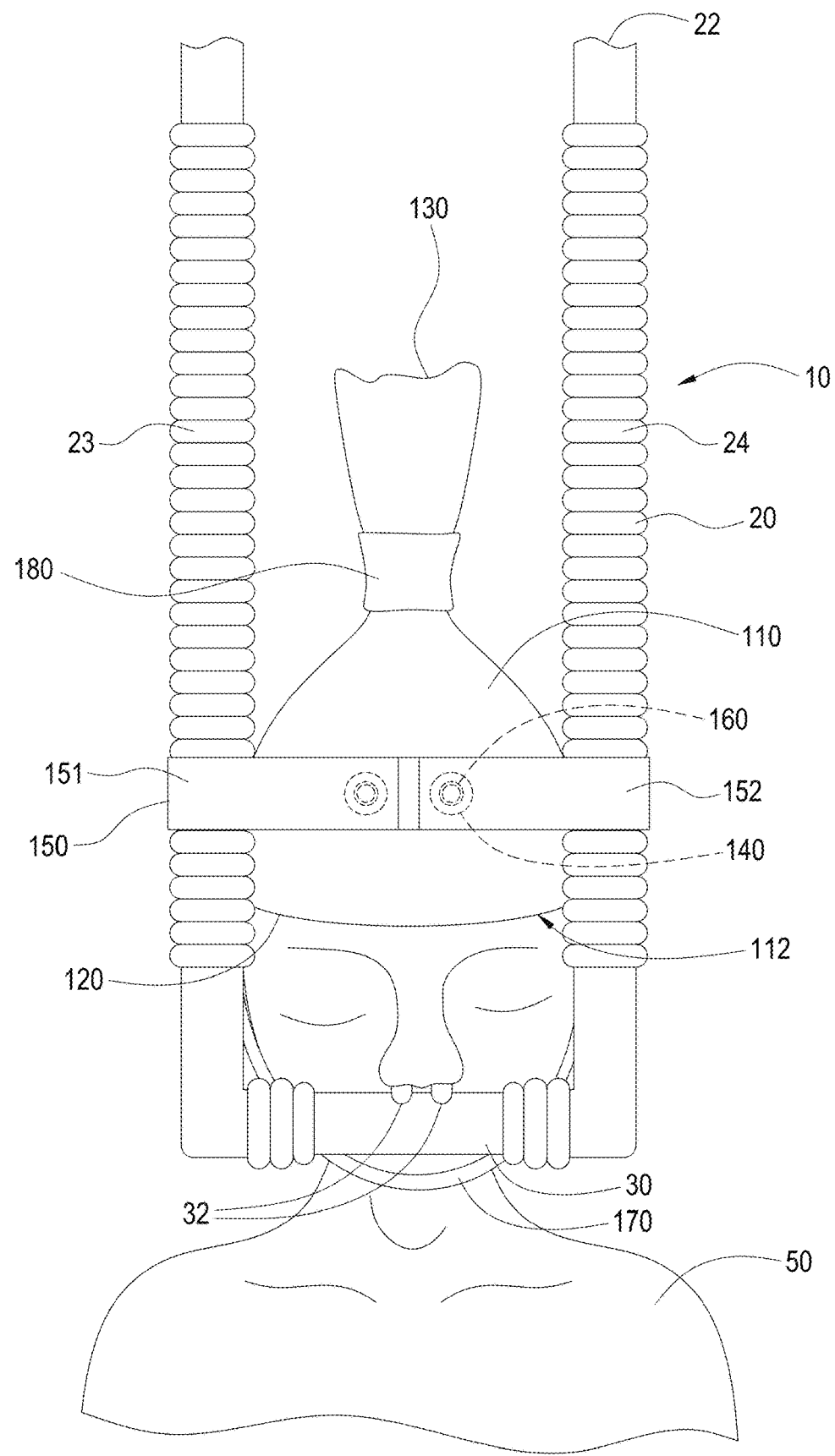
FIG. 3 is a schematic view, illustrating the infant and child bonnet according to a second embodiment of the present invention.

In the embodiment shown in FIG. 3, the first connection portion 140 and the second connection portion 160 can be male-female buckles or male-female snap fasteners. To be specific, the first connection portion 140 and the second connection portion 160 can be two fasteners having a concave shape and a protruding shape to be coupled with each other to join two separate objects. The male-female snap fasteners are used in a similar manner to that described in the above-mentioned embodiment, so a detailed description is omitted for brevity.

To use the infant and child bonnet 100, first the cap body 110 is put on the head of the infant/child 50, and then the elastic fixing band 150 is used to fix the breathing tube 10 to the cap body 110, the first arm 151 configured to extend around the cap body 110 and flexibly fix the first inlet tube 23 of the breathing tube 10 between the elastic fixing band 150 and the cap body 110, the second arm 152 configured to extend around the cap body 110 and flexibly fix the second inlet tube 24 of the breathing tube 10 between the elastic fixing band 150 and the cap body 110. Alternatively, first the elastic fixing band 150 is used to fix the breathing tube 10 to the cap body 110, and then the cap body 110 is put on the head of the infant/child 50, the usage method may change according to circumstances or needs. Therefore, the infant and child bonnet 100 suits various head sizes and shapes of the infant/child 50 and can effectively fix the breathing tube 10 without displacement or detachment.

Furthermore, the cap body 110 further includes an elastic tying band 180 disposed adjacent to the second opening 130 for tying the cap body 110. The cap body 110 preferably wraps the head of the infant/child 50 and only exposes a face of the infant/child 50. Furthermore, the elastic tying band 180 can be selectively utilized to tie an upper portion of the cap body 110. Therefore, the infant and child bonnet 100 of the present invention is prevented from falling off or slipping off the head. In addition to that, the infant and child bonnet 100 can improve comfort for the infant/child 50 who wears it and keep his/her head warm.

Moreover, the cap body 110 further includes a chin band 170. The chin band 170 is connected in an integral manner or in a separate manner to a bottom (i.e. the first opening 120) of the cap body 110. The chin band 170 assists in fixing the cap body 110 to the head of the infant/child 50 and further prevents leakage of oxygen from his/her mouth by keeping the mouth closed, thereby facilitating efficient treatment.

It is to be understood that the above descriptions are merely the preferable embodiment of the present invention and are not intended to limit the scope of the present invention. Equivalent changes and modifications made in the spirit of the present invention are regarded as falling within the scope of the present invention.

What is claimed is:

1. An infant and child bonnet, for securing a breathing tube, comprising:
   a cap body, the cap body including a first opening and a second opening, the first opening formed at a first end of the cap body and the second opening formed at a second end of the cap body;
   a first connection portion fixed to a front side of the cap body;
   an elastic fixing band fixed to a back side of the cap body, the elastic fixing band comprising a first arm and a second arm, the first arm and the second arm including a second connection portion, the first arm configured to extend around the cap body and flexibly fix a first inlet tube of the breathing tube between the elastic fixing band and the cap body, the second arm configured to extend around the cap body and flexibly fix a second inlet tube of the breathing tube between the elastic fixing band and the cap body; and
   the second connection portion configured to connect with the first connection portion.

2. The infant and child bonnet of claim 1, wherein the cap body further includes an accommodating space communicating with the first opening and the second opening.

3. The infant and child bonnet of claim 2, wherein the accommodating space is configured such that a head of an infant or a child is inserted into the accommodating space from the first opening, the accommodating space suits various head sizes and shapes, and a size of the first opening is bigger than or the same to a size of the second opening.

4. The infant and child bonnet of claim 1, wherein the elastic fixing band is stitched in place between the first opening and the second opening.

5. The infant and child bonnet of claim 1, wherein the cap body further includes a chin band, and the chin band is flexibly connected to a bottom of the cap body.

6. The infant and child bonnet of claim 5, wherein the chin band is integrally formed with the cap body.

7. The infant and child bonnet of claim 1, further comprising an elastic tying band disposed adjacent to the second opening for tying the cap body.

8. The infant and child bonnet of claim 1, wherein the first connection portion and the second connection portion consist of male-female Velcro fasteners, male-female adhesive strips, male-female buckles, or male-female snap fasteners.

9. The infant and child bonnet of claim 1, wherein the cap body consists of knitted wool or knitted threads.

* * * * *